United States Patent
Genese et al.

(10) Patent No.: US 6,482,190 B1
(45) Date of Patent: Nov. 19, 2002

(54) OUTLET TUBE DEVICE FOR URINARY DRAINAGE BAG

(75) Inventors: Joseph Nicholas Genese, Covington, GA (US); Igor Blinow, Gainesville, GA (US); Randall Roy Pfutzenreuter, Danbridge, TN (US); John F. Jankowski, Dunwoody, GA (US)

(73) Assignee: C.R. Bard Inc,, Murray Hill, NJ (US)

( * ) Notice: Subject to any disclaimer, the term of this patent is extended or adjusted under 35 U.S.C. 154(b) by 0 days.

(21) Appl. No.: 09/639,227

(22) Filed: Aug. 15, 2000

Related U.S. Application Data

(62) Division of application No. 08/796,569, filed on Feb. 6, 1997, now Pat. No. 6,132,407.

(51) Int. Cl.$^7$ ................................................. A61M 1/00
(52) U.S. Cl. ..................... 604/327; 604/317; 604/323; 604/324; 251/9; 251/146; 222/103; 24/16 R
(58) Field of Search .................. 604/317, 323, 604/327, 331, 335, 349, 353, 406, 408; 251/9, 146, 319; 222/103, 559; 29/16 R

(56) References Cited

U.S. PATENT DOCUMENTS

| | | | |
|---|---|---|---|
| 823,068 A | * 6/1906 | Mosley | |
| 3,061,263 A | * 10/1962 | Butler | 251/9 |
| 3,131,812 A | * 5/1964 | Constant | 206/69 |
| 3,228,574 A | 1/1966 | Patch | |
| 3,345,980 A | * 10/1967 | Coanda | 128/2 |
| 3,415,299 A | 12/1968 | Hinman, Jr. et al. | |
| 3,568,965 A | * 3/1971 | Clark | 248/95 |
| 3,661,143 A | * 5/1972 | Henkin | 128/2 |
| 3,698,681 A | * 10/1972 | Lacey | 251/10 |
| 3,713,622 A | * 1/1973 | Dinger | 251/10 |
| 3,822,052 A | * 7/1974 | Lange | 251/10 |
| 3,823,716 A | 7/1974 | Hale | |
| 3,831,453 A | 8/1974 | McWhorter | |
| 3,942,228 A | 3/1976 | Buckman et al. | |
| 3,990,680 A | 11/1976 | Messey | |
| 4,055,179 A | 10/1977 | Manschot et al. | |
| 4,095,589 A | 6/1978 | Manschot et al. | |

(List continued on next page.)

FOREIGN PATENT DOCUMENTS

WO    WO 9317642    9/1995

*Primary Examiner*—Dennis Ruhl
*Assistant Examiner*—Michael Bogart
(74) *Attorney, Agent, or Firm*—Kilpatrick Stockton

(57) ABSTRACT

An improved outlet tube device for a urinary drainage bag is disclosed wherein an outlet valve mechanism is contained with a rigid housing fixed securely to the drainage bag, rather than just being clamped to the outlet tubing, and thus cannot become separated from the bag. The outlet valve can be opened only by positive action on the part of the medical care personnel, thereby assuring that urine will be discharged only in a controlled manner. Further, because the valve mechanism does not require that a substantial length of tubing with a freely movable end be used in conjunction with the outlet port, there is no need to engage the free end of the tubing with a keeper. Thus the possibility of the tubing springing back to its straight configuration and flicking residual urine on the attending medical personnel is eliminated. In one embodiment the outlet tube device comprises a pinchcock-type valve which is fixedly mounted to the bag and which is normally operative to clamp off the outlet tube. In a second embodiment the outlet tube device comprises a syringe-type fitting which is fixedly mounted to the bag. Depressing the syringe plunger closes the valve, and retracting the plunger opens the valve to permit fluid to be discharged through the outlet tube. In a third embodiment, a hose clamp is contained within a rigid housing and is selectively operative to clamp a hose to prevent fluid flow therethrough.

9 Claims, 11 Drawing Sheets

U.S. PATENT DOCUMENTS

| | | | |
|---|---|---|---|
| 4,134,573 A | | 1/1979 | Messinger |
| 4,247,076 A | * | 1/1981 | Larkin .......................... 251/7 |
| 4,280,498 A | | 7/1981 | Jensen |
| 4,291,706 A | | 9/1981 | Voges et al. |
| 4,306,705 A | | 12/1981 | Svensson |
| 4,417,892 A | * | 11/1983 | Meisch ...................... 604/323 |
| 4,460,362 A | | 7/1984 | Bates |
| 4,462,510 A | | 7/1984 | Steer |
| 4,534,766 A | * | 8/1985 | Steer et al. ................. 604/323 |
| 4,540,156 A | | 9/1985 | Cross |
| 4,581,763 A | | 4/1986 | Olsen |
| D283,918 S | * | 5/1986 | Jacobson .................... D24/27 |
| 4,589,626 A | * | 5/1986 | Kurtz et al. .................. 251/10 |
| 4,625,735 A | | 12/1986 | Sherlock et al. |
| 4,629,159 A | | 12/1986 | Wellenstam |
| RE32,338 E | * | 1/1987 | Alexander et al. ............ 294/16 |
| 4,634,437 A | | 1/1987 | Lowthian |
| 4,643,389 A | * | 2/1987 | Elson et al. .................. 251/10 |
| 4,673,161 A | * | 6/1987 | Flynn et al. .................. 251/10 |
| 4,702,740 A | | 10/1987 | Bates |
| 4,723,950 A | * | 2/1988 | Lee ............................ 604/322 |
| 4,728,324 A | | 3/1988 | Steigerwald et al. |
| 4,736,925 A | * | 4/1988 | Kamstrup-Larsen et al. .. 251/10 |
| 4,802,650 A | * | 2/1989 | Stricker ...................... 251/117 |
| 4,807,622 A | * | 2/1989 | Ohkaka et al. ............. 128/305 |
| 4,815,477 A | | 3/1989 | McWhorter et al. |
| 4,820,284 A | | 4/1989 | Hauri |
| 4,834,702 A | * | 5/1989 | Rocco ......................... 604/43 |
| 4,909,478 A | | 3/1990 | Steer |
| 4,944,485 A | * | 7/1990 | Daoud et al. .................. 251/9 |
| 4,983,172 A | * | 1/1991 | Steer et al. ................. 604/332 |
| 5,026,359 A | | 6/1991 | Burroughs |
| 5,035,399 A | * | 7/1991 | Rantanen-Lee ............. 251/10 |
| 5,083,741 A | * | 1/1992 | Sancoff ......................... 251/9 |
| 5,135,199 A | | 8/1992 | Cross et al. |
| 5,259,588 A | | 11/1993 | Crosby et al. |
| 5,318,546 A | * | 6/1994 | Bierman ..................... 604/250 |
| 5,401,256 A | * | 3/1995 | Stone et al. ................. 604/250 |
| 5,429,615 A | * | 7/1995 | Starchevich ................ 604/246 |
| 5,496,299 A | * | 3/1996 | Felix et al. ................. 604/319 |
| 5,593,392 A | * | 1/1997 | Starchevich ................ 604/246 |
| 5,616,138 A | * | 4/1997 | Propp ......................... 604/317 |
| 5,640,742 A | * | 6/1997 | White et al. ................. 24/3.12 |
| 5,725,515 A | * | 3/1998 | Propp ......................... 604/317 |
| 5,827,230 A | * | 10/1998 | Bierman ..................... 604/174 |
| 5,902,294 A | | 5/1999 | Edwards |
| 6,089,527 A | * | 7/2000 | Utterberg ....................... 251/4 |
| 6,132,407 A | * | 10/2000 | Genese et al. ............. 604/327 |
| 6,132,408 A | * | 10/2000 | Lutz ........................... 604/335 |
| 6,113,062 A | * | 11/2000 | Schnell et al. ................ 251/10 |
| 6,196,519 B1 | * | 3/2001 | Utterberg ..................... 251/10 |
| 6,213,140 B1 | * | 4/2001 | Ploeger ......................... 137/1 |
| 6,213,979 B1 | * | 4/2001 | Bierman ..................... 604/174 |
| 6,234,448 B1 | * | 5/2001 | Porat ........................... 251/10 |
| 6,261,254 B1 | * | 7/2001 | Baron et al. ................. 602/323 |

\* cited by examiner

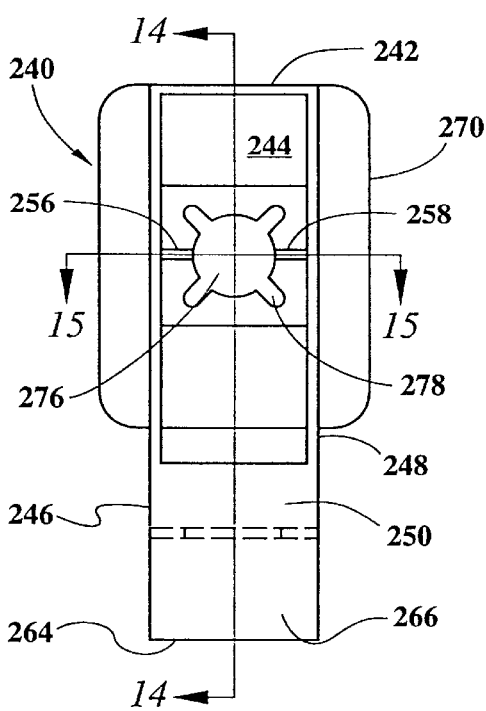
*FIG. 13*
*FIG. 14*
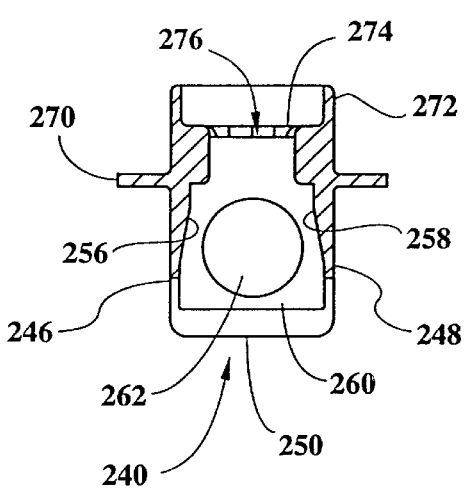
*FIG. 15*
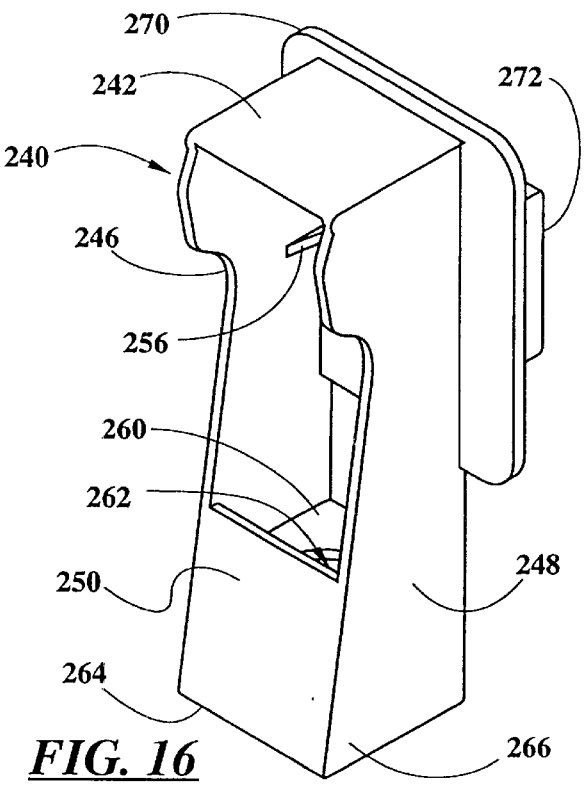
*FIG. 16*

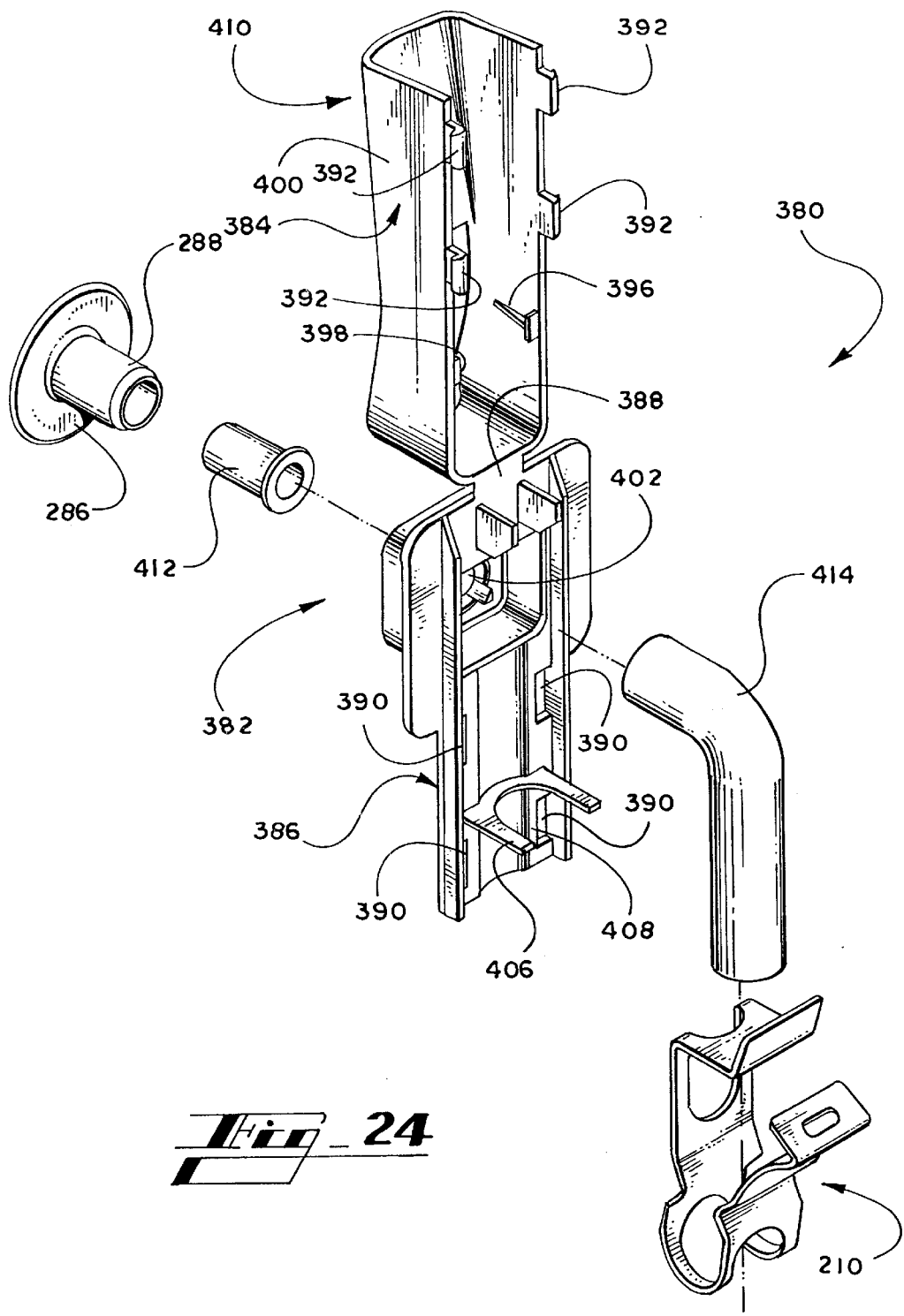
Fig_24

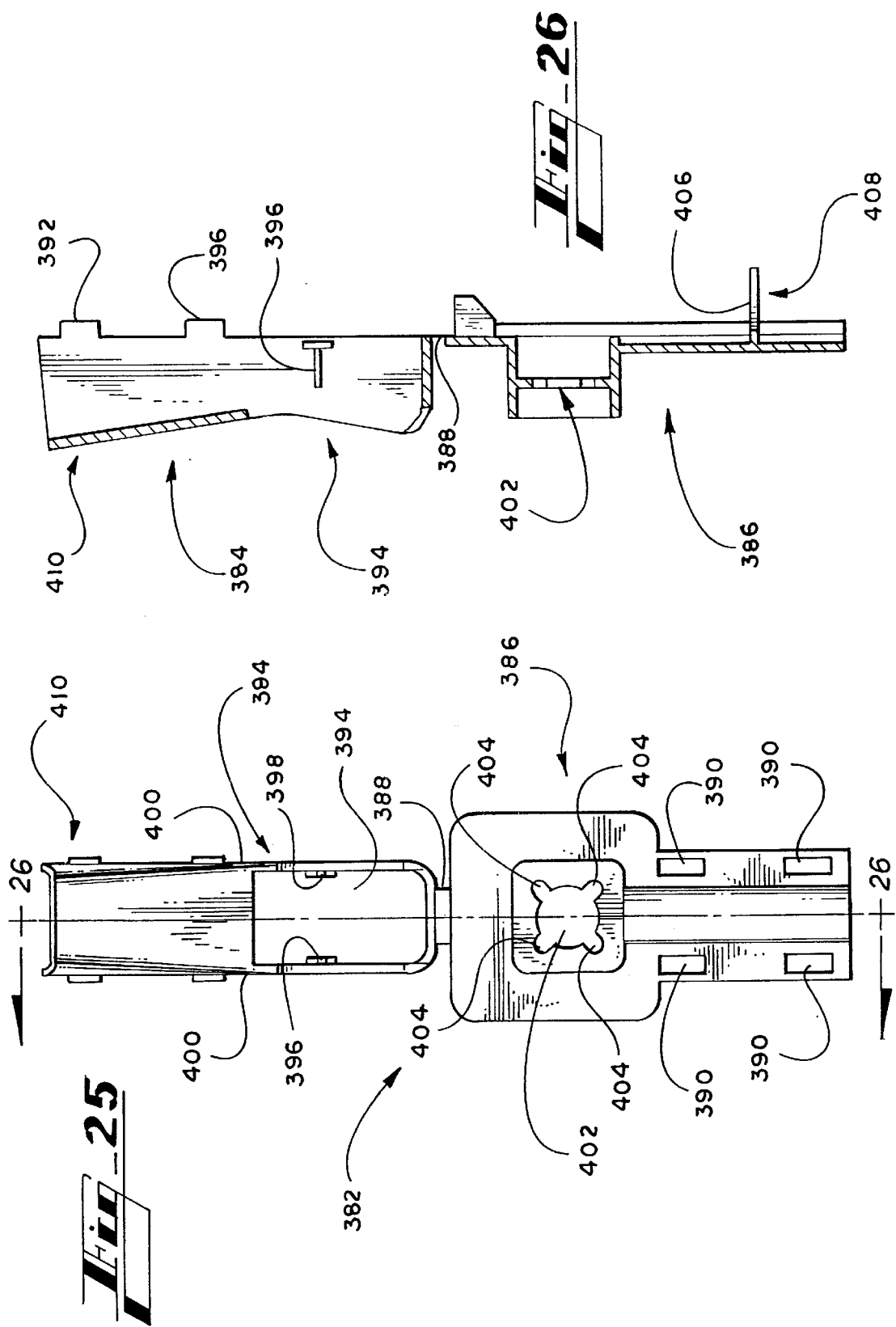

OUTLET TUBE DEVICE FOR URINARY DRAINAGE BAG

CROSS-REFERENCE TO RELATED APPLICATIONS

This application is a division of U.S. patent application Ser. No. 08/796,569, filed Feb. 6, 1997, now issued as U.S. Pat. No. 6,132,407.

TECHNICAL FIELD

The present invention relates generally to urine collection products and relates more specifically to a urinary drainage bag with an improved means for controlling discharge of bag contents through an outlet port.

BACKGROUND OF THE INVENTION

It is well known to discharge urinary catheters into urinary drainage bags for collecting urine from catheterized patients. Such bags are typically attached to the hospital bed below the level of the patient such that urine flows into the bag under force of gravity. To permit fluid to be drained from the bag, either when the bag becomes overly full or when a specimen is needed, an outlet port is provided adjacent the lower end of the bag. Typically the outlet port comprises a rubber outlet tube having one end in fluid communication with the interior of the bag. To prevent fluid from flowing through the outlet tube, a clamp or "pinchcock" is provided which slides over the end of the tube and clamps the walls of the tube to occlude its lumen. Fluid is discharged through the outlet port by releasing the clamp from the outlet tube. When the outlet port is not in use, the free end of the tube engages a keeper mounted on the bag to retain the tube closely against the side of the bag.

With such prior art drainage bag outlet tube devices, when the free end of the flexible outlet tube is disengaged from its keeper, if the tube is not handled properly the resiliency of the rubber tube will cause the tube to spring outward. In such a case there is the attendant possibility that residual droplets of urine in the end of the tube will flick onto the attending medical personnel. In addition, with some prior art devices there is even the possibility that the clamp which normally closes the outlet tube can be accidentally pulled off of the tube. The resulting uncontrolled flow of urine from the outlet tube is at best messy and can cause urine to splash on the attending medical personnel.

Thus there is a need for an outlet tube device for a urinary drainage bag which avoids the possibility of the outlet tube springing outward in such a manner as to flick droplets of residual urine on the attending medical personnel.

There is a further need for an outlet tube device for a urinary drainage bag which satisfies the foregoing need and wherein the mechanism which prevents the flow of urine through the outlet port cannot accidentally become disengaged from the bag.

Because urinary drainage bags must be attended by healthcare personnel who have many other duties, it is imperative that any improved urinary drainage bag be capable of being operated quickly, preferably a single step operation which can be accomplished with only one hand. Furthermore, because of the single-patient nature of urine collection bags, it is important that the urinary drainage bag be low cost and easy to manufacture.

Thus there is a need for an outlet tube device for a urinary drainage bag which is splashless, which is inexpensive to manufacture yet operates quickly, which requires only a single step to operate, and which can be operated with only one hand.

SUMMARY OF THE INVENTION

As will be seen, the present invention overcomes these and other disadvantages associated with prior art urinary collection bags. Stated generally, the present invention comprises a urinary collection bag in which the an outlet tube mechanism which prevents the flow of urine through the outlet port cannot accidentally become disengaged from the bag. Thus the possibility of the mechanism becoming disengaged from the bag and permitting uncontrolled flow of urine from the outlet port is eliminated. In addition, the urinary collection bag of the present invention eliminates the need to store the free end of the outlet tube in a keeper when not in use, thereby eliminating the possibility of the outlet tube springing outward in such a manner as to flick droplets of residual urine on the attending medical personnel. Further the device is inexpensive to manufacture and can be operated quickly with only one hand.

Stated somewhat more specifically, the outlet tube devices of the present invention overcome these problems by providing an outlet valve mechanism which is fixed securely to the drainage bag, rather than just being clamped to the tubing, and thus cannot be separated from the bag. The outlet valve can be opened only by positive action on the part of the medical care personnel, thereby assuring that urine will be discharged only in a controlled manner. Further, because the valve mechanism used in lieu of the conventional clamp does not require that a substantial length of tubing be used in conjunction with the outlet port, there is no need to engage the free end of the tubing with a keeper. Thus the possibility of the tubing springing back to its straight configuration and flicking residual urine on the attending medical personnel is eliminated.

The first embodiment of the improved outlet tube device comprises a "pinchcock" arrangement wherein spring-loaded jaws clamp the outlet tubing and prevent fluid flow through the tubing. The pinchcock is mounted to the drainage bag such that it cannot accidentally be pulled away from the bag. Urine can be discharged through the tubing only by the medical care personnel squeezing the upper ends of the clamp jaws together, thereby opening the jaws of the clamp and permitting fluid to flow through the tube. A latch is provided which can be engaged when the jaws are in their spread configuration to maintain the pinchcock in the open position without the requirement that someone continually manually compress the jaws.

A second embodiment comprises a syringe-like configuration which mounts directly to the retainer outlet port affixed to the drainage bag and defines a passageway in fluid communication with the interior of the drainage bag. The outlet port device comprises a plunger having a stopper at its lower end which occludes the passageway when the plunger is depressed, thereby preventing fluid flow. To discharge urine from the drainage bag, the medical care personnel must affirmatively extend the plunger, thereby retracting the stopper and permitting fluid flow through the passageway.

A third embodiment comprises a rigid housing mounted over the outlet port of the drainage bag. A length of rubber hose extends from the outlet port through the housing. A spring steel clamp is contained within the housing and is operatively associated with the hose to clamp the hose to prevent fluid flow therethrough. The clamp can be opened as needed to permit fluid to be discharged through the hose.

A first alternate design of the third embodiment comprises a hinged door at the lower front end of the rigid housing to facilitate assembly. A second alternate design of the third embodiment comprises a two-part housing wherein the entire front housing portion is hinged to the rear housing portion to facilitate assembly.

Thus it is an object of the present invention to provide an improved urinary drainage bag.

It is a further object of the present invention to provide a urinary drainage bag wherein the mechanism which prevents the flow of urine through the outlet port cannot accidentally become disengaged from the bag.

Another object of the present invention is to provide a urinary drainage bag which avoids the possibility of the outlet tube springing outward in such a manner as to flick droplets of residual urine on the attending medical personnel.

Still another object of the present invention is to provide a urinary drainage bag which meets the foregoing criteria and which can be operated quickly, in a single step, and with only one hand.

It is yet another object of the present invention to provide a urinary drainage bag which meets the foregoing criteria and is inexpensive to manufacture.

Other objects, features, and advantages of the present invention will become apparent upon reading the following specification, when taken in conjunction with the drawings and the appended claims.

BRIEF DESCRIPTION OF THE DRAWINGS

FIG. 13 is a front elevation view of a housing which comprises another component of the third embodiment of an outlet port valve means according to the present invention.

FIG. 14 is a side cutaway view of the housing of FIG. 13 taken along line 14—14 of FIG. 13.

FIG. 15 is a bottom cutaway view of the housing of FIG. 13 taken along line 15—15 of FIG. 13.

FIG. 16 is a perspective view of the housing of FIG. 13.

FIG. 24 is an exploded perspective view of another alternate embodiment of a housing for use with the clamp of FIGS. 9–12.

FIG. 25 is an elevation view of the housing of the embodiment of FIG. 24.

FIG. 26 is a side cutaway view as seen along line 26—26 of FIG. 25.

DETAILED DESCRIPTION OF THE DISCLOSED EMBODIMENT

Figure 1:
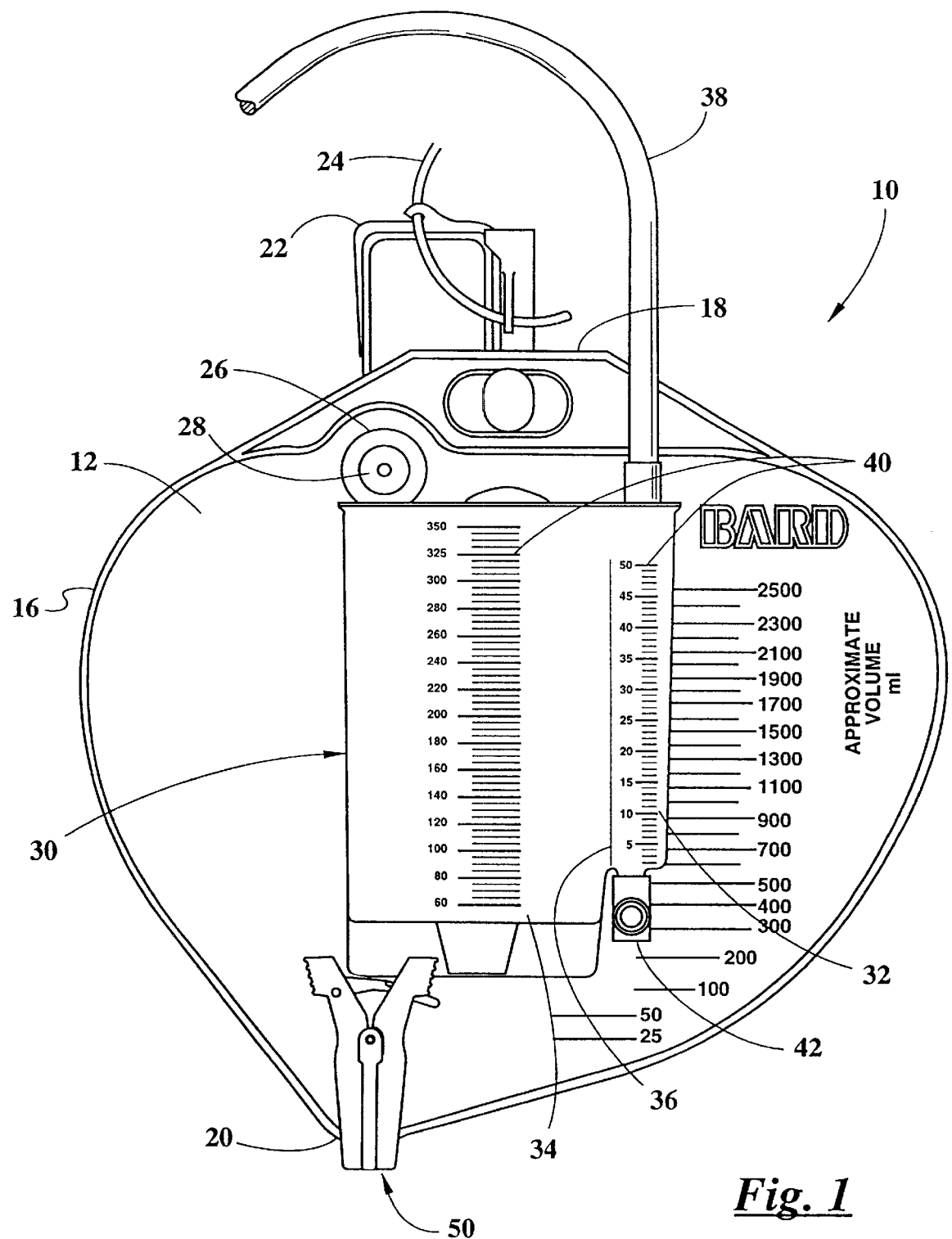
FIG. 1 is a plan view of a urinary drainage bag comprising an improved drainage outlet port according to the present invention.

Referring now to the drawings, in which like numerals indicate like elements throughout the several views, FIG. 1 discloses a urinary drainage bag 10. The urinary drainage bag 10 is of conventional construction and comprises a front sheet 12 and a back sheet 14 of a flexible, fluid-impervious material. The front and back sheets 12, 14 are bonded at their marginal edges 16 to form a fluid-tight chamber therebetween.

The urinary drainage bag 10 has an upper end 18 and a lower end 20. A hook 22 is located at the upper end 18 of the drainage bag 10 to provide a means by which the bag can be hung during use. A string hanger 24 is also provided at the upper end 18 of the drainage bag 10 for use on those occasions where no suitable structure exists for the hook 22 to engage. A vent 26 with suitable filtration means 28 vents the interior of the bag 10 to the atmosphere. A urine meter 30 is mounted to the front sheet 12 of the bag 10. The urine meter 30 is a rigid container of plastic or other suitable material and comprises a first compartment 32 and a second compartment 34 separated by a wall 36. A tubing 38 empties into the first compartment 32. The wall 36 is of a height such that when the first compartment 32 is filled with a fluid, fluid will overflow into the second compartment 34. Graduated markings 40 on the front face of the meter 30 indicate the volume of fluid in the meter. A septum 42 at the bottom of the first compartment 32 provides a sample port by which a urine specimen may be withdrawn from the meter 30 for analysis. The meter 30 is in fluid communication with the interior of the drainage bag 10 by means of a port (not shown), whereby the contents of the meter can be emptied into the bag 10 by tilting the meter.

Figures 2, 3, 4:
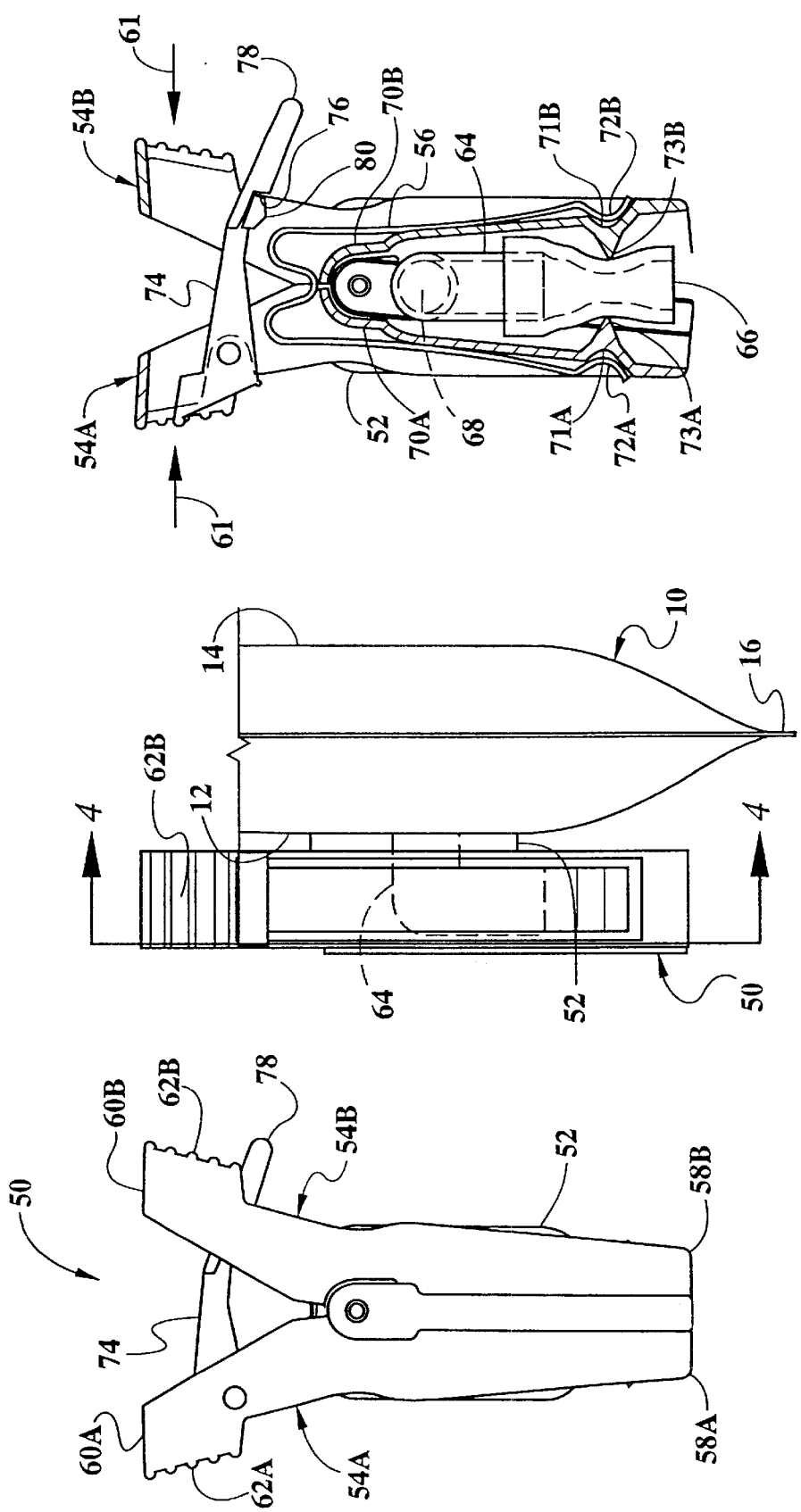
FIG. 2 is a plan view of a first embodiment of an outlet port valve means according to the present invention.
FIG. 3 is a side view of the valve means of FIG. 2.
FIG. 4 is a front cutaway view of. the valve means of FIG. 2 taken along section line 4—4 of FIG. 2.

Referring now to FIGS. 2–4, an outlet tube device 50 in the form of a pinchcock clamp is located at the lower end 20 of the urinary drainage bag 10. The outlet tube device 50 includes a main body portion 52 fixedly mounted to the bag 10. A pair of opposed jaws 54A, 54B are pivotably mounted to the main body portion 52. The jaws 54A, 54B are spring-loaded by means of a spring 56 so that the lower ends 58A, 58B of the jaws are biased together. The lower ends 58A, 58B of the jaws 54A, 54B can be opened by squeezing the upper ends 60A, 60B of the jaws together in the direction indicated by the arrows 61 in FIG. 4. The upper ends 60A, 60B of the jaws 54A, 54B are provided with grooved gripping surfaces 62A, 62B to facilitate manipulation of the pivotable jaws.

An outlet duct 64 is formed on the main body portion 52 of the outlet tube device 50. A discharge tube 66 comprising a length of flexible tubing is attached to the lower end of the outlet duct 64. An outlet port 68 is formed in the front sheet 12 of the bag 10 in register with the passageway of the outlet duct 64, whereby the interior of the bag 10 is in fluid communication with the discharge tube 66.

The jaws 54A, 54B each have interior ribs 70A, 70B formed thereon. Recesses 71A, 71B are formed on the exterior edge of the ribs 70A, 70B for receiving inwardly projecting, arcuate segments 72A, 72B of the spring 56 to couple the spring 56 to the jaws 54A, 54B. Formed on the interior edge of the ribs 70A, 70B are inwardly facing, mutually cooperating prongs 73A, 73B which engage opposing sides of the discharge tube 66. When the jaws 54A, 54B are closed, the force of the spring 56 causes the prongs 73A, 73B to completely occlude the discharge tube 66. When the jaws 54A, 54B are opened by squeezing the upper ends 60A, 60B of the jaws together, the prongs 73A, 73B separate sufficiently to permit the lumen of the discharge tube 66 to open.

A latch 74 is pivotably mounted to the jaw 54A adjacent its upper end 60A. The latch comprises a flange 76 formed adjacent its free end 78. A keeper 80 is formed adjacent the upper end 60B of the opposite jaw 54B. The flange 76 is configured to cooperatively engage the keeper 80 when the upper ends 60A, 60B of the jaws are squeezed together to maintain the jaws in their open position.

Operation of the outlet tube device 50 will now be explained with further reference to FIGS. 2–4. When the outlet tube device is in its normal closed position, as depicted in FIG. 2, the latch 74 is disengaged from the keeper 80, and the spring 56 biases the lower ends 58A, 58B of the jaws 54A, 54B together. In this position the prongs 73A, 73B completely pinch off the discharge tube 66, preventing the flow of fluid through the tube. When it is necessary to discharge a portion or all of the contents of the bag 10, the user places thumb and forefinger on the grooved gripping surfaces 62A, 62B at the upper ends 60A, 60B of the jaws 54A, 54B and squeezes the upper ends of the jaws together in the direction indicated by the arrows 61 in FIG. 4. This squeezing action opens the lower ends 58A, 58B of the jaws 54A, 54B, retracting the prongs 73A, 73B away from the discharge tube 66. The discharge tube 66 opens as a result of its resilient construction and permits fluid to flow therethrough. Fluid thus exits the bag 10 through the outlet port 68 in the bag, flows through the outlet duct 64, and is discharged through the discharge tube 66. Meanwhile, the flange 76 of the latch 74 at the upper end of the jaws 54A, 54B may be engaged with the keeper 80, as shown in FIG. 4, to maintain the jaws in their open configuration without the necessity for continued manual pressure on the jaws.

When it is desired to discontinue fluid flow through the outlet tube device 50, the user again grasps the grooved gripping surfaces 62A, 62B at the upper ends 60A, 60B of the jaws 54A, 54B with thumb and forefinger and squeezes the upper ends of the jaws together. While maintaining inward pressure on the upper ends 60A, 60B of the jaws 54A, 54B, the free end 78 of the latch 74 is lifted with a free finger of the gripping hand to disengage the flange 76 from the keeper 80. Inward pressure on the upper ends 60A, 60B of the jaws 54A, 54B is now relaxed, permitting the lower ends 58A, 58B of the jaws to close. As the jaws close, the prongs 73A, 73B are once again brought into contact with the discharge tube 66, pinching off the tube and stopping fluid flow therethrough.

Figure 5:
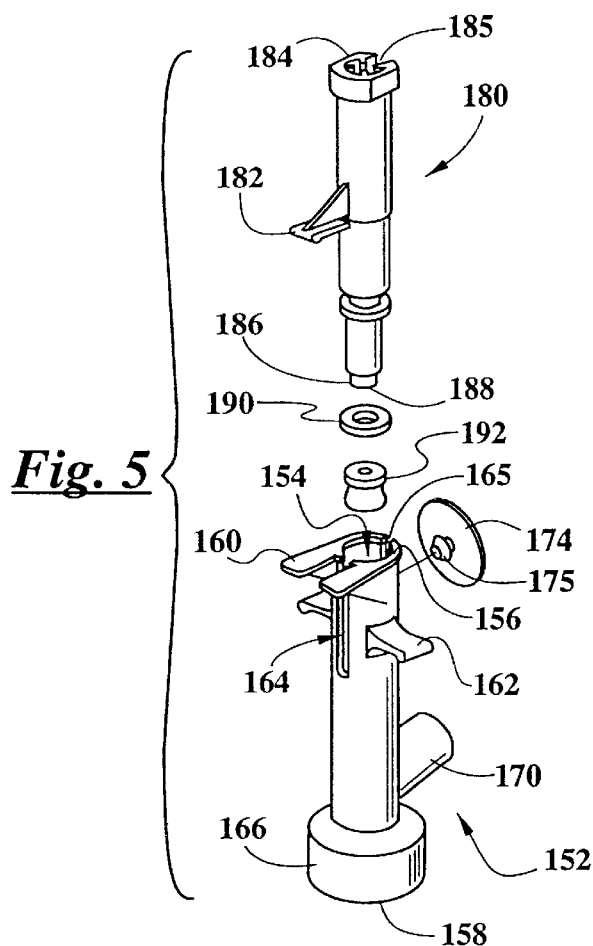
FIG. 5 is an exploded perspective view of a second embodiment of an outlet port valve means according to the present invention.
Figure 6:
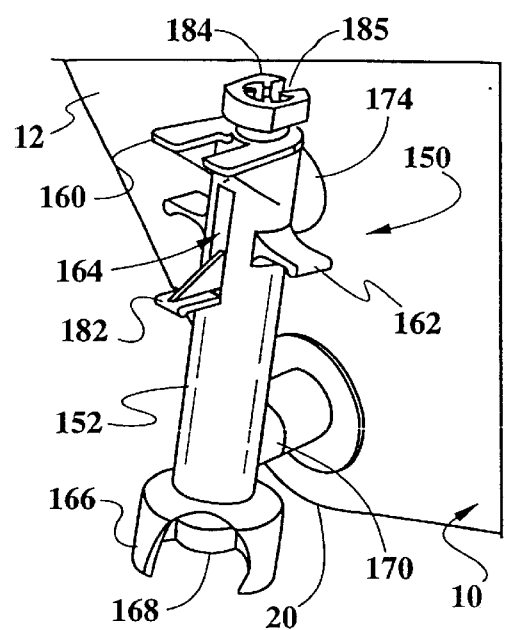
FIG. 6 is a perspective view of the valve means of FIG. 5 shown assembled and mounted to a urinary drainage bag.

Referring now to FIGS. 5 and 6, an alternate embodiment of an outlet tube device 150 is shown. The outlet tube device 150 comprises a body 152 generally in the shape of an elongated cylinder. The body 152 of the disclosed embodiment is formed from clear plastic or other suitable material. A bore 154 is formed through the body from its upper end 156 to its lower end 158. A first set of flanges 160 projects forward from the upper end 156 of the body 152. A second set of flanges 162 projects laterally one from either side of the body 152 at a location spaced below the first set of flanges 160. A front longitudinal slot 164 is formed in the front of the body 152 between the first set of flanges 160, and a rear longitudinal slot 165 is formed in the rearward surface of the body 152 opposite the front slot 164. The purpose and function of the flanges 160, 162 and slots 164, 165 will be described below.

A skirt 166 is formed at the lower end 158 of the body 152. The skirt 166 envelopes a discharge tube 168 (FIG. 6) which comprises an extension of the bore 154. As can perhaps best be seen in FIGS. 7 and 8, the discharge tube 168 tapers inwardly and thus is smaller in diameter than the bore 154.

The body 152 further comprises a rigid tube 170 extending rearward from a location adjacent the lower end 158 of the body. The tube 170 includes a bore 172 (FIGS. 7–8) communicating with the bore 154 at right angles thereto. The tube 170 fits over a port fitting (not shown) adjacent the lower end 20 of the urinary drainage bag 10 such that the tube 170, and hence the bore 154, are in fluid communication with the interior of the bag 10. The upper end of the body 152 is mounted to the bag 10 by means of a dart 174 which is bonded to the front sheet 12 of the bag. The dart 174 includes a forward projecting flange 175 which engages the slot 165 in the rear surface of the body 152. An outlet port 176 is formed in the front sheet 12 of the bag 10 in register with the bore 172 of the tube 170, whereby the interior of the bag 10 is in fluid communication with the discharge tube 168.

The outlet tube device 150 further comprises a plunger 180 formed of plastic or other suitable material coaxially slidably disposed within the fore 154 of the body 152. A forward projecting flange 182 is formed on the plunger 180 at a location spaced downward from the upper end 184 of the plunger. The flange 182 rides within the vertical slot 164 formed in the body 152 as the plunger moves axially within the bore 154. A longitudinal channel 185 is formed in the rearward portion of the plunger 180 and is located coincident with the rear longitudinal slot 165 in the rear surface of the body 152. The purpose of the channel 185 is to clear the flange 175 of the dart 174 which is captured within the rear longitudinal slot 165 in the rear surface of the body 152.

A nipple 186 is formed at the lower end 188 of the plunger 180. An O-ring 190 is circumferentially disposed around the plunger 180 at a location spaced upward from the lower end 188 of the plunger. A stopper 192 is attached to the nipple 186 at the lower end 188 of the plunger. The O-ring 190 is dimensioned to sealingly engage the walls of the bore 154 of the body 152. The stopper 192 is somewhat smaller than the bore 154 but is dimensioned to sealingly engage the inwardly tapered walls of the discharge tube 168 when the plunger is depressed.

Figure 7:
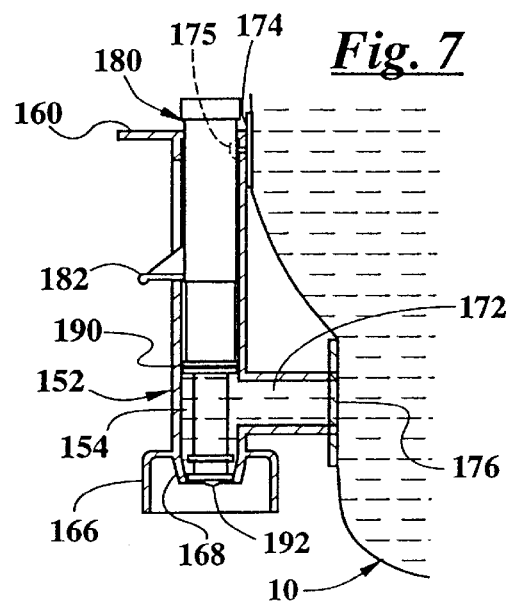
FIG. 7 is a side cutaway view showing the valve means of FIG. 5 in a closed configuration.
Figure 8:
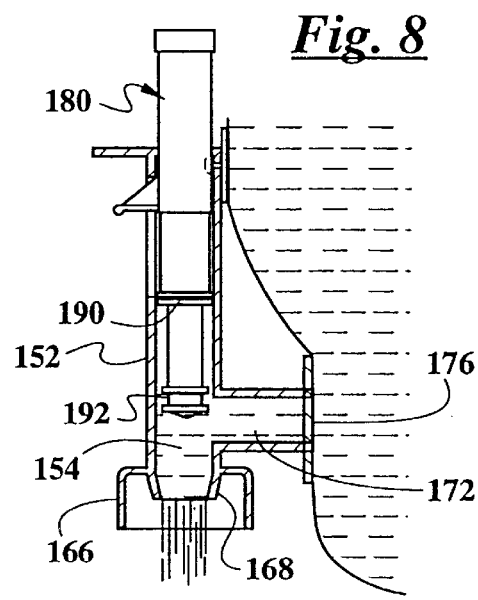
FIG. 8 is a side cutaway view showing the valve means of FIG. 5 in an open configuration.
Figure 9:
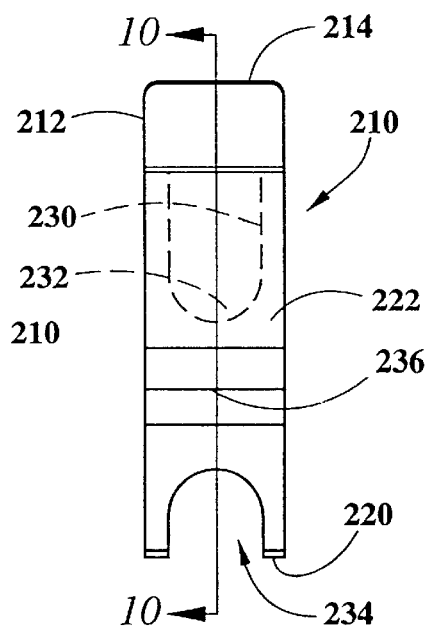
FIG. 9 is a front elevation view of a clamp which comprises a component of a third embodiment of an outlet port valve means according to the present invention.
Figure 10:
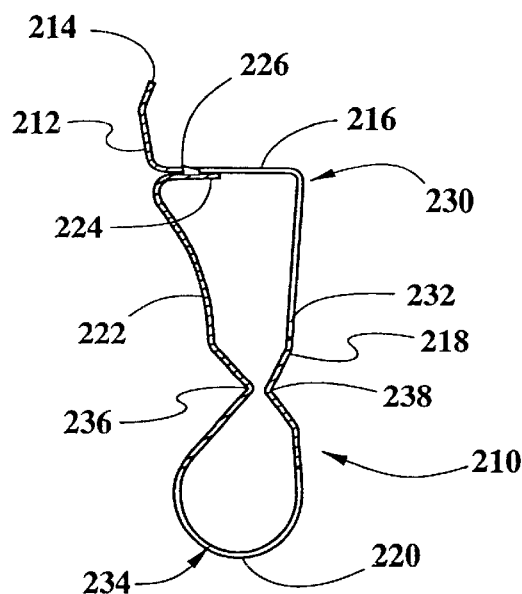
FIG. 10 is a side view of the clamp of FIG. 9 showing the clamp in a closed position.
Figure 11:
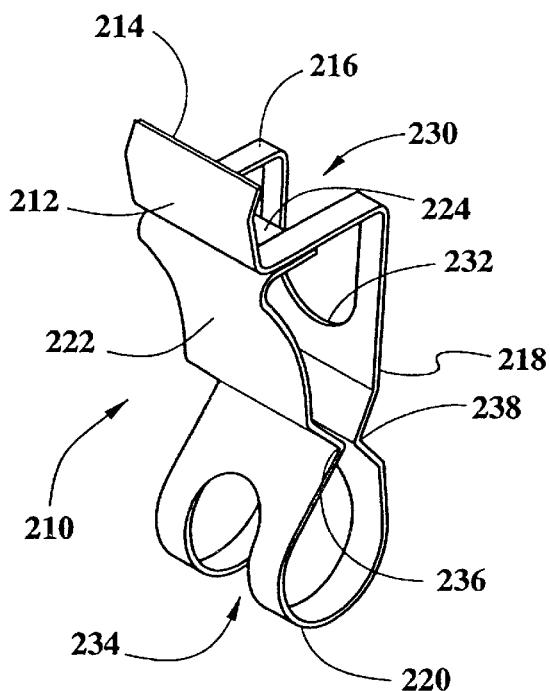
FIG. 11 is a perspective view of the clamp of FIG. 9.

Operation of the outlet tube device 150 will now be explained with reference to FIGS. 7 and 8. The plunger 180 is normally depressed to the position shown in FIG. 7 to prevent the discharge of fluid from the outlet tube device 150. In this depressed position, the stopper 192 sealingly engages the inwardly tapered walls of the discharge tube 168. Similarly the O-ring 190 sealingly engages the walls of the bore 154 of the body 152 to prevent fluid from leaking upward into the bore 154. When it is desired to discharge some or all of the contents of the bag through the outlet tube device 150, the user places a thumb on top of the first set of flanges 160, places a forefinger beneath the forward projecting flange 182 of the plunger 180, and squeezes. The plunger 180 is thereby retracted to a raised position as shown in FIG. 8, wherein the stopper 192 is disengaged from the tapered walls of the discharge tube 168 and permits fluid to pass out of the bag 10 through the outlet port 176, through the bore 172 of the tube 170, into the bore 154 of the body, and downward to exit through the discharge tube 168. In this position the O-ring 190 continues to seal the walls of the bore 154 of the body 152 to prevent fluid from leaking upward into the bore 154. To shut off the flow of fluid through the outlet tube device 150, the user places a thumb atop the upper end 184 of the plunger 180, places first and second fingers beneath the second set of flanges 162 projecting laterally one from either side of the body 152, and depresses the plunger as one would depress the plunger of a syringe. The plunger 180 is advanced until the stopper 192 sealingly engages the tapered walls of the discharge tube 168, shutting off the flow of fluid through the outlet tube device 150.

The second embodiment provides the advantage that the outlet tube device 150 takes the form of a syringe, a device with which medical personnel are already familiar, and hence operation of the device 150 is intuitive.

FIGS. 9–22 illustrate a third embodiment of an improved outlet tube device for a urinary drainage bag according to the present invention. Referring first to FIGS. 9–12, a clamp member 210 is comprised of spring steel or other suitable material. The clamp member 210 comprises an upstanding tab 212 adjacent its upper end 214. The lower end of the tab 212 is connected to an upper leg 216. The rearward end of the upper leg 216 is connected to a downward extending back leg 218. At the lower end of the back leg 218, the lower end 220 of the clamp 210 curves upward, and a front leg 222 extends upward therefrom. At the upper end of the front leg 222, a reentrant rib 224 extends rearward.

A portion of the reentrant rib 224 is punched upward to form an upwardly extending flange 226. A cooperating slot or cutout 230 is formed in a corresponding portion of the upper leg 216. The front leg 222 of the clamp 210 can be pushed rearward until the upwardly extending flange 226 catches the forward end of the cutout 230 in the upper leg 216 to retain the clamp 210 in a closed configuration. The clamp member 210 is configured to assume the expanded configuration shown in FIG. 12 normally and can be compressed to assume the closed configuration shown in FIG. 10. The flange 226 and cooperating slot 230 retain the clamp 210 in its closed configuration, while disengaging the flange 226 from its cutout 230 causes the clamp 210 to return to its normal, open configuration.

The cutout 230 extends all the way to the back end of the upper leg 216 and extends part way down the back leg 218 of the clamp 210, where it terminates in a semicircular lower end 232. In a like manner an arcuate cutout 234 is formed in the lower end 220 of the clamp 210. The purpose and function of the cutouts 230, 234 will be explained hereinbelow.

Figure 12:
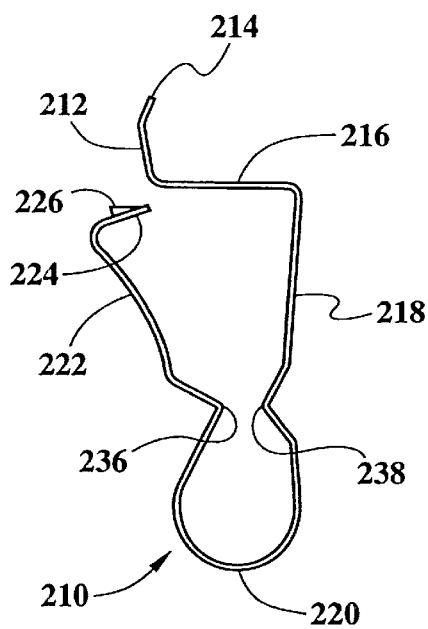
FIG. 12 is a side view of the clamp of FIG. 9 showing the clamp in an open position.

A rearward projecting pinch jaw 236 is formed in the front leg 222 of the clamp 210. A cooperating forward extending pinch jaw 238 is formed in the back leg 218 of the clamp 210. As can be seen by a comparison of FIGS. 10 and 12, the pinch jaws 236, 238 are disposed closely together when the clamp 210 is in its closed configuration (FIG. 10), while the pinch jaws 236, 238 are further separated when the clamp 210 is in its open configuration (FIG. 12).

A housing 240 is shown in FIGS. 13–16. The housing 240 comprises a top wall 242, a back wall 244, opposed side walls 246, 248, and a front wall 250, the back, side, and front walls 244, 246, 248, and 250 depending downward from corresponding peripheral edges of the top wall 242.

A vertically elongated window 252 is formed in the front wall 250 of the housing 240. A pair of opposed clamp positioning and securing ribs 256, 258 extend inward of the housing from the side walls 246, 248. A lower transverse wall 260 having a circular opening 262 formed therethrough is formed within the housing 240 adjacent its lower end 264. The lower end 264 of the housing 240 is open, and the lowermost portions of the back wall 244, side walls 246, 248, and front wall 250 form a skirt 266 around the periphery of the housing 240 adjacent its lower end 264.

At the upper end of the housing 240 a pair of wings 270 project outward of the side walls 246, 248. A hollow sleeve 272 projects rearward from the back wall and communicates with the interior of the housing 240. In the disclosed embodiment the sleeve 272 is essentially square in cross-section. A vertical wall 274 is formed across the interior of the sleeve 272. An opening 276 is formed through the vertical wall 274. The opening 276 is generally circular with a plurality of radial cutouts 278 extending outward therefrom.

Figure 18:
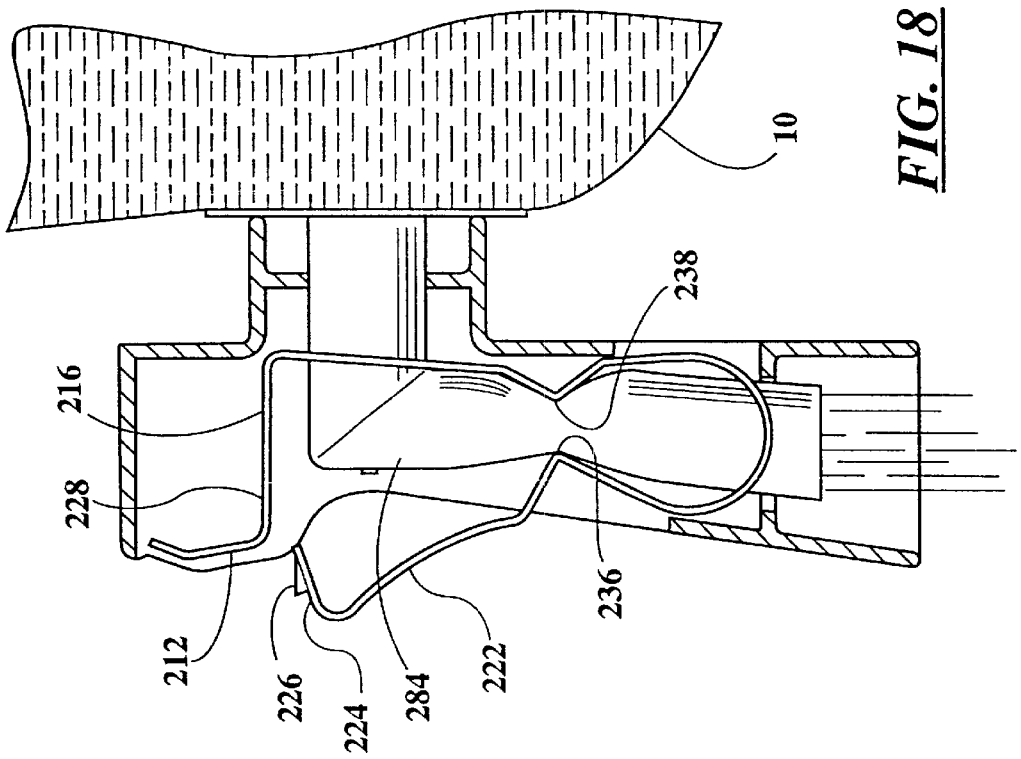
FIG. 18 is a side cutaway view of the outlet port valve means of FIG. 17 showing the valve in an open position.
Figure 17:
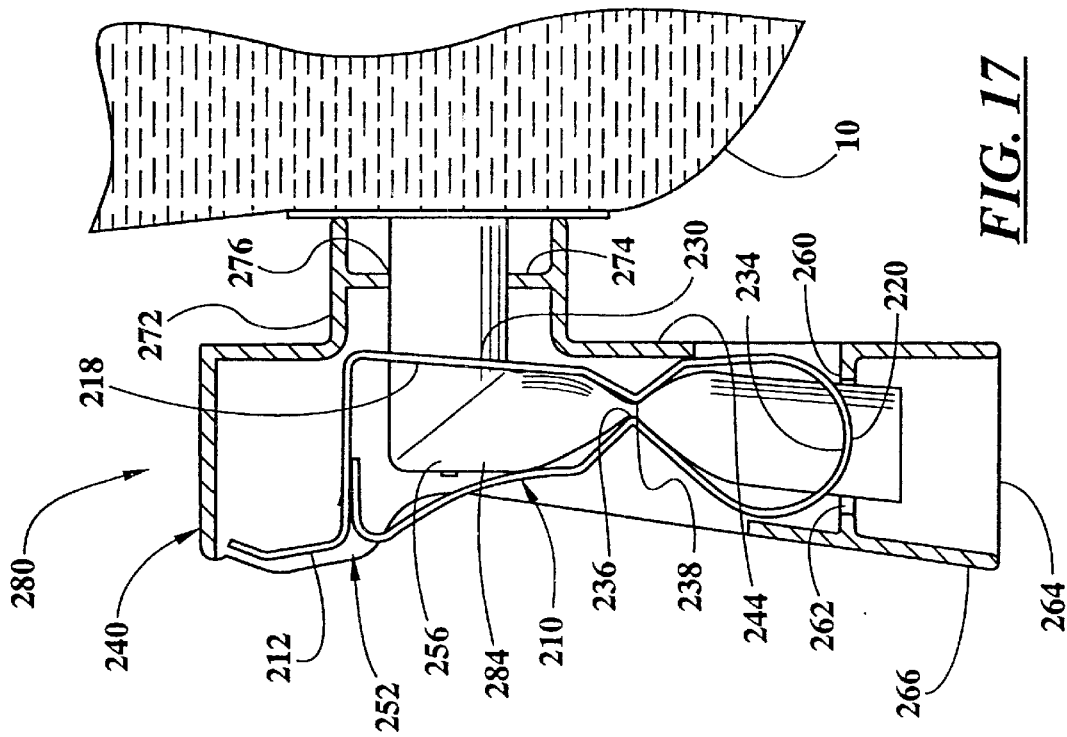
FIG. 17 is a side cutaway view of the third embodiment of an outlet port valve means according to the present invention, showing the valve in a closed position.

FIGS. 17 and 18 show an outlet tube device 280 comprising the clamp 210 and housing 240. The outlet tube device 280 is attached to the lower end of a urinary drainage bag 10. A length of rubber tubing 284 is mounted to the urinary drainage bag 10 with the interior of the tubing 284 in fluid communication with the interior of the urinary drainage bag 10. The tubing 284 extends forward through the sleeve 272 and extends through the opening 276 in the vertical transverse wall 274. The tubing then bends 90° downward and extends through the opening 262 in the lower transverse wall 260 of the housing 240. The tubing 284 terminates within the skirt 266 at the lower end 264 of the housing 240.

The clamp 210 is located within the housing 240 in operative engagement with the tubing 284. The tubing 284 passes forward through the cutout 230 in the rear of back leg 218 of the clamp 210. The downward extending portion of the tubing 284 passes between the pinch jaws 236, 238 and extends through the arcuate cutout 234 in the lower end 220 of the clamp 210.

The clamp 210 is disposed within the housing 240 with the tab 212 of the clamp 210 located in the upper portion of the window 252 of the housing 240. The lower end 220 of the clamp 210 is located adjacent the lower transverse wall 260 of the housing 240, and the back leg 218 of the clamp 210 lies adjacent the back wall 244 of the housing 240. The clamp 210 is maintained in position by mechanical engagement with the clamp positioning and securing ribs 256, 258 formed on the interior walls of the housing 240.

With the clamp 210 in its closed configuration, as shown in FIG. 17, the pinch jaws 236, 238 clamp the tubing 284, occluding the lumen of the tubing and preventing the flow of fluid therethrough. When it is desired to discharge fluid from the urinary drainage bag through the outlet tube device, a user presses the tab 212 of the clamp 210 inward. The inward force on the tab 212 causes the upper leg 216 of the clamp 210 to pivot upward, disengaging the flange 226 on the reentrant rib 224 from the cutout 230 in the upper leg 216 of the clamp 210. As the front leg 222 springs forward, the pinch jaws 236, 238, separate, permitting the tubing 284 to open and fluid to flow therethrough, as shown in FIG. 18. When it is desired to stop the discharge of fluid from the urinary drainage bag 10, the user presses the front leg 222 inward until the upwardly projecting flange 226 on the reentrant rib 224 once again engages the cutout 230 in the upper leg 216 of the clamp 210. In this configuration the pinch jaws 236, 238 once again clamp off the tubing 284, preventing the further discharge of fluid.

It will be appreciated that the wings 270 formed at the upper end of the housing 240 facilitate the exertion of inward pressure on the tab 212 and front leg 222 of the clamp 210. The user can place his or her first and second fingers behind the wings 270, preferably from above the housing 240, one finger on either side of the sleeve 272, and use the downward extending thumb of the same hand to exert pressure on the tab 212 or front leg 222, as appropriate. Thus one handed operation of the device 280 is facilitated.

Figure 19:
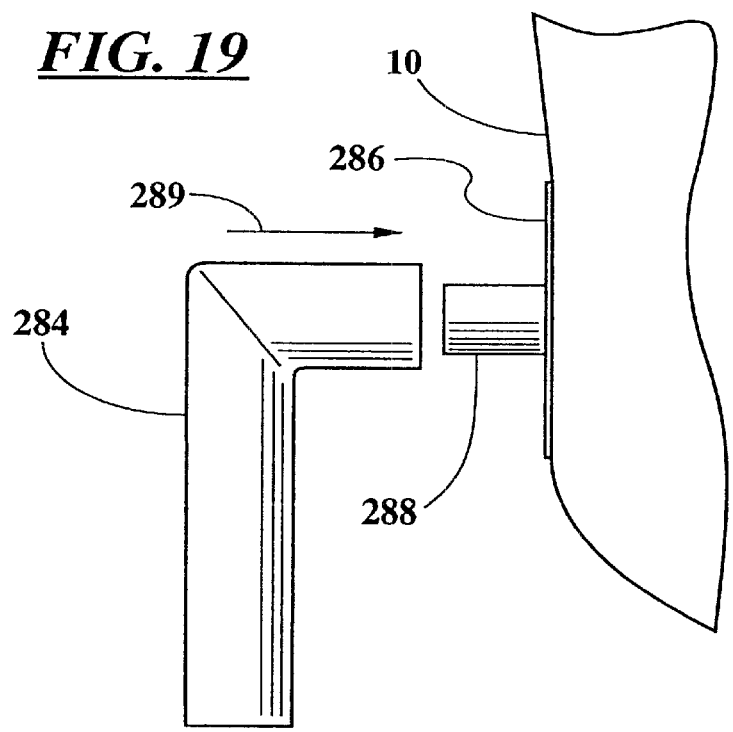
FIG. 19 is a side view depicting a first step in the assembly of the outlet port valve means of FIG. 17 wherein a rubber tubing is attached to a urinary drainage bag.

FIGS. 19–22 illustrate the assembly of the outlet tube device 280. Referring first to FIG. 19, a fitting 286 is bonded to the surface of the urinary drainage bag 10 adjacent the lower end of the bag. The fitting 286 comprises a nipple 288 extending forward therefrom. One end of the tubing 284 is advanced in the direction indicated by the arrow 289 over the nipple 288 and is retained thereon by an interference fit.

Figure 20:
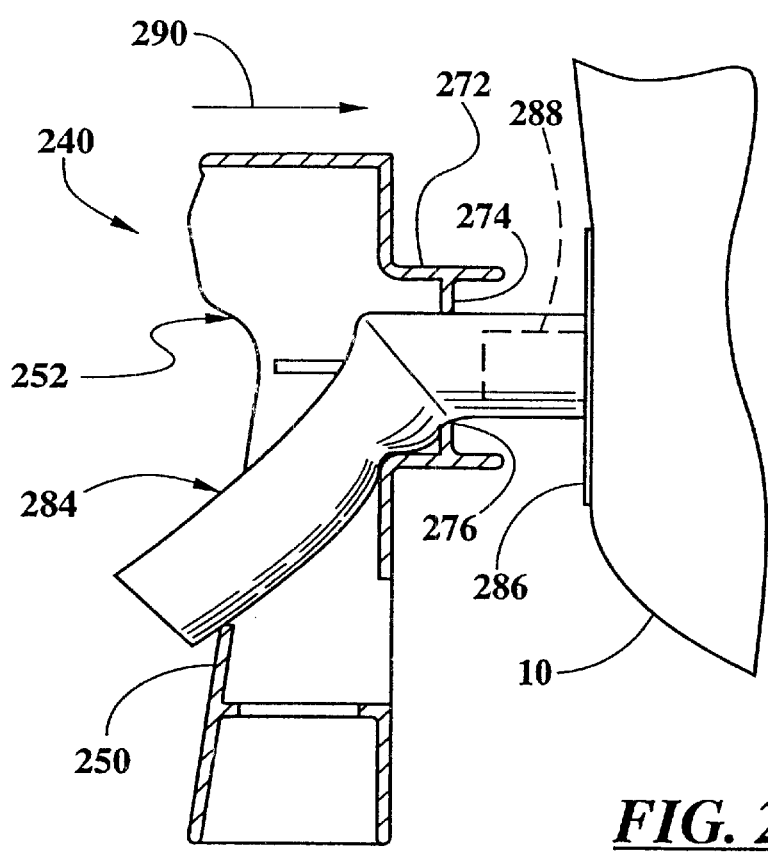
FIG. 20 is a side view depicting a second step in the assembly of the outlet port valve means of FIG. 17 wherein the housing of FIG. 13 is mounted to the urinary drainage bag.

Referring now to FIG. 20, the housing 240 is advanced in the direction indicated by the arrow 290 over the free end of the tubing 284, with the tubing being received through the opening 276 in the vertical transverse wall 274 across the sleeve 272. As the housing 240 is advanced further, the free end of the tubing 284 projects through the window 252 in the front wall 250 of the housing. The housing 240 continues to be advanced until the walls defining the opening 276 advance beyond the end of the nipple 288. The housing 240 is held in place by the interference fit between the walls defining the opening 276, the tubing 284, and the nipple 288. To accommodate a tight fit, some of the material comprising the tubing 284 is displaced into the radial cutouts 278 (FIG. 13) which extend outward from the circular opening 276. This displacement of the tubing material into the radial cutouts 278 also provides the advantage of preventing the housing 240 from rotating with respect to the nipple 288.

Figure 21:
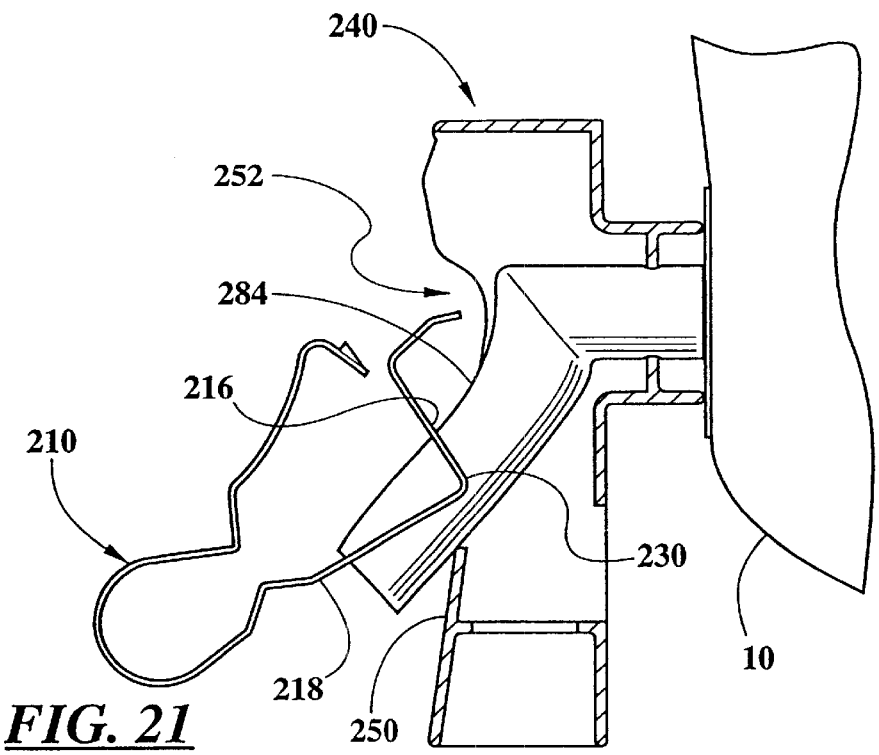
FIG. 21 is a side view depicting a third step in the assembly of the outlet port valve means of FIG. 17 wherein the clamp of FIG. 9 is assembled onto the rubber tubing.
Figure 22:
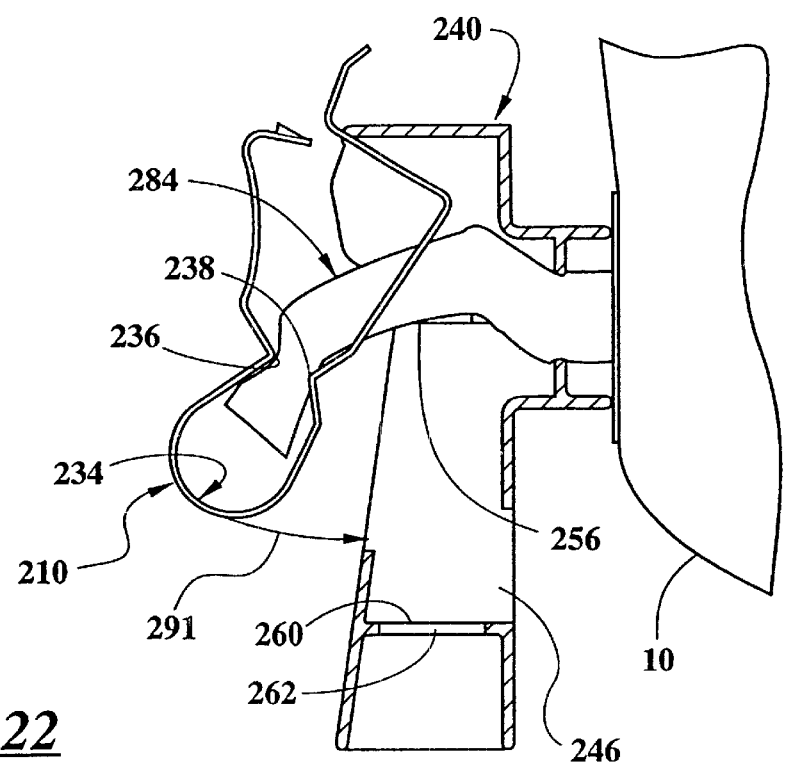
FIG. 22 is a side view depicting a fourth step in the assembly of the outlet port valve means of FIG. 17 showing the clamp of FIG. 9 being positioned within the housing.

With the housing 240 and tubing 284 thus mounted to the bag 10, and with the tubing 284 projecting forward through the window 252 in the front wall 250 of the housing, the clamp 210 is installed onto the tubing. The clamp 210 is advanced over the free end of the tubing 284 with the tubing being received through the cutout 230 in the upper and back legs 216, 218 of the clamp 210, as shown in FIG. 21. With the clamp 210 in its opened configuration, the free end of the tubing 284 is advanced downward between the pinch jaws 236, 238 of the clamp 210. As this is being accomplished, the clamp 210 is maneuvered, as indicated by the arrow 291, through the window in the front wall 250 of the housing 240, as seen in FIG. 22. The free end of the tubing 284 is then advanced through the arcuate cutout 234 in the lower end 220 of the clamp 210 and then through the circular opening 262 in the lower transverse wall 260 of the housing 240. Simultaneously the clamp 210 is positioned within the housing 240 against the clamp positioning and securing ribs 256, 258 extending inward from the side walls 246, 248 of the housing. The clamp 210 is captured between the clamp positioning and securing ribs 256, 258 by an interference fit to prevent the clamp from backing out of the housing during use.

It will be appreciated that while the outlet tube device 270 of the third embodiment works on the principle of a spring clamp clamping off a rubber tubing in much the same manner done by prior art devices, the outlet tube device 270 provides significant advantages over prior art devices. Because the tubing 284 is essentially held immobile by the rigid housing 240, the possibility of the rubber tube springing free and flicking residual urine from the end of the tube onto attending medical personnel is eliminated. The device is easily operated with one hand, and the termination of the tube within the skirt at the lower end of the housing prevents the attending medical personnel from accidentally contacting the end of the tubing. Finally, the clamp 210 is disposed within the housing 240 and cannot become disengaged from the tubing 284 so long as the tubing is constrained within the housing 240.

Figure 23:
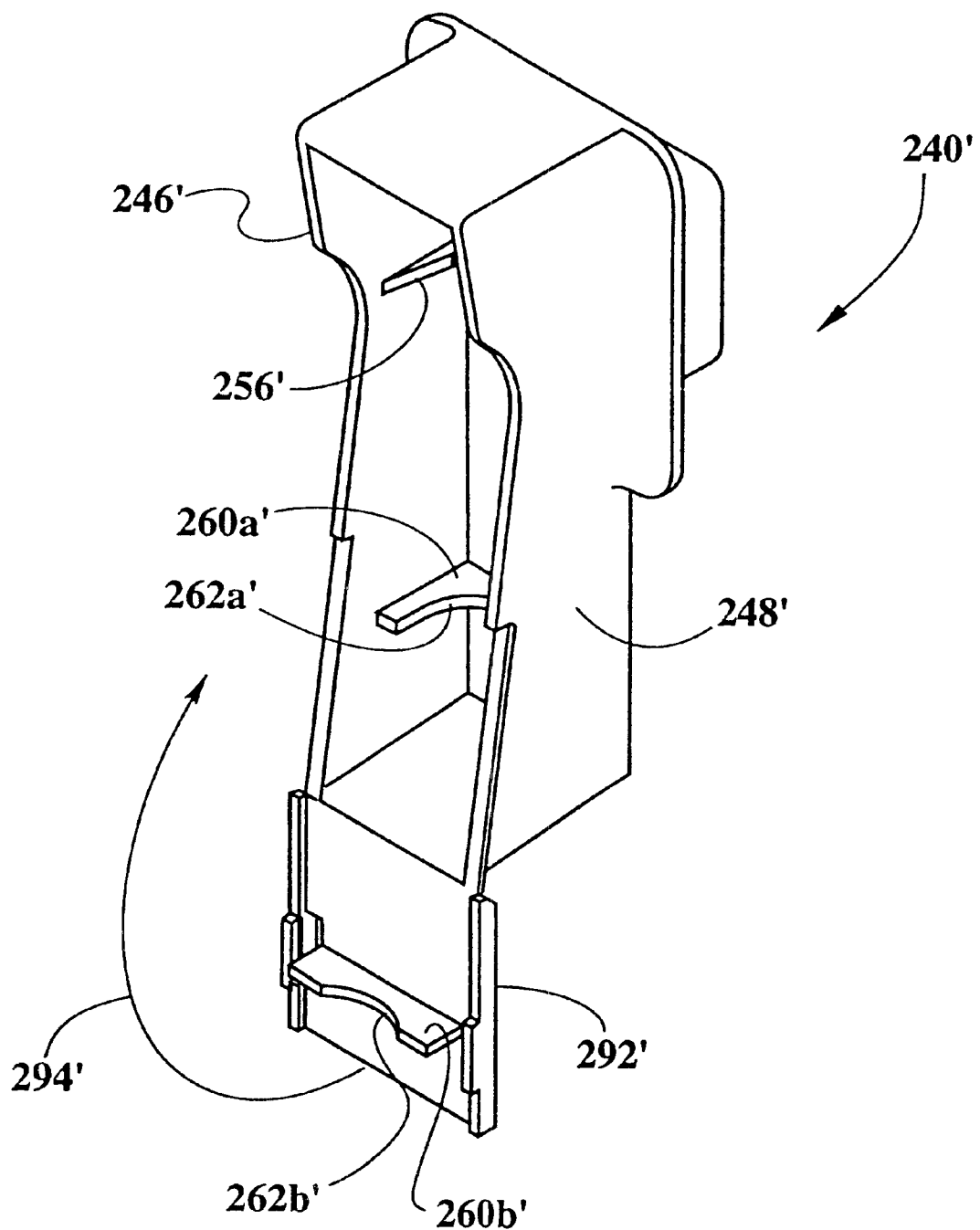
FIG. 23 is a perspective view of an alternate embodiment of a housing for use with the clamp of FIGS. 9–12.

An alternate design of a housing 240' shown in FIG. 23 provides a variation of the third embodiment of the outlet tube device 280. The housing 240' is in most respects similar to the housing 240 of FIGS. 13–16 and includes clamp positioning and securing ribs 256', 258' (only the rib 256' is visible in FIG. 23) extending inward from the side walls 246', 248' of the housing. However, a hinged door 292' is formed in the lower portion of the front wall 250. Further, the lower transverse wall 260' is divided into a rear transverse wall section 260a' mounted within the housing 240' and a forward transverse wall section 260b', formed on the interior surface of the hinged door 292'. A first arcuate wall 262a' formed on the rear transverse wall section 260a' mates with a second arcuate wall 262b' formed on the forward transverse wall section 260b' to form a circular opening 262' when the hinged door 292' is closed.

The housing 240' with the hinged door 292' is assembled together with the clamp 210 of FIGS. 9–12 to form an outlet tube device. The housing 240' and clamp 210 are assembled in the same manner as hereinabove described with respect to the housing 240 with one important exception. It will be recalled that assembly of the clamp 210 to the housing 240 requires that the lower end of the tubing 284 be maneuvered through the circular opening 262 in the lower transverse wall 260 simultaneous with trying to fit the clamp 210 through the window 252 in the front wall 250 of the housing 240. In contrast, to assemble the clamp 210 to the housing 240', the hinged door 292' is opened, permitting the lower end of the tubing 284 with clamp 210 attached to pivot into position against the first arcuate wall 262a' formed on the rear transverse wall section 260a'. Then the hinged door 292' is pivoted closed in the direction indicated by the arrow 294', bringing the forward transverse wall section 260b' with second arcuate wall 262b' into position over the lower end of the tubing 284, capturing the tubing 284 and clamp 210 in place.

Another alternate design of an outlet tube device 380 is shown in FIGS. 24–26. The outlet tube device 380 includes a housing 382 which comprises a front portion 384 and a rear portion 386 connected at their upper ends by a hinge 388. Slots 390 are formed adjacent the edges of the rear portion 386 of the housing 382. Cooperating tabs 392 are formed to project rearward from the front portion 384 of the housing 382 to engage the slots 390 in the rear portion of the housing to lock the housing portions together.

The housing 382 includes a vertically elongated window 394 in its front portion 384. A pair of opposed clamp positioning and securing ribs 396, 398 extend inward of the front portion 384 of the housing 382 from the side walls 400 of the front portion 384. Formed in the rear portion 386 of the housing 382 is a generally circular opening 402 with a plurality of radial cutouts 404 extending outward therefrom. A lower transverse wall 406 having a semi-circular opening 408 therethrough extends forward from the rear portion 386 of the housing 382 adjacent its lower end. When the housing portions 384, 386 are closed, the lower wall 402 fits within the front portion 384 of the housing 382. Also when the housing is closed, the lower walls of the front housing portion 384 form a skirt 410.

The outlet tube device 380 also comprises a fitting 286 which is mounted to the front face of a bag 10. A nipple 288 extend forward from the fitting 286. A bushing 412 fits within the tubular nipple structure to provide additional stiffness and structural support. The forward end of the fitting 286 fits through the circular opening 402 in the rear portion 386 of the housing 382. A 90° angled flexible tubing 414 then slides over the forward end of the nipple 288 of the fitting 286 to place the lumen of the tubing 414 in fluid communication with the interior of the bag 10. A clamp 210 is advanced upward over the lower end of the tubing 414, and the downward extending leg of the tubing 414 is received within the semi-circular-opening 408 in the lower transverse wall 406. When thus assembled the clamp 210 resides above the lower transverse wall 406. The front portion 384 of the housing 382 is then swung downward against the rear portion 386, the tabs 392 on the front housing portion 384 engaging the slots 390 in the rear housing portion 386 to lock the housing portions together. With the front housing portion 384 thus closed, the lower end of the tubing 414 resides within the skirt 410 formed by the lower end of the housing 382. Also with the front housing portion 384 closed, the clamp positioning and securing ribs 396, 398 retain the clamp 210 in place.

Once assembled, the outlet tube device 380 works essentially identically to the outlet tube device 240 hereinabove described. An operator actuates the clamp 210 to permit flow or to shut off flow of fluid through the tubing 414. Access to the clamp 210 is by way of the elongated window 394 in the front portion 384 of the housing 382. The skirt 410 formed by the lower portion of the housing 382 protects the discharge end of the tubing 414 from accidental contact by attending health care personnel.

The arrangement by which the entire front portion 384 of the housing 382 is hinged, rather than only a partial portion of the front portion as in the housing 240', facilitates assembly of the outlet tube device 380. Rather than having to assemble the tubing 414 and clamp 210 onto the fitting 286 with the side walls of the housing in the way, the tubing and clamp are assembled against the essentially planar rear housing portion 386, and the front housing portion 384 with side walls is pivoted into place only after the tubing and clamp are assembled onto the fitting.

All of the outlet tube devices 50, 150, 280, and 380 of the present invention provide numerous advantages over prior art outlet tube devices. Since the outlet tube devices 50, 150, 280, and 380 are all fixedly mounted to the front surface of the bag 10, the devices cannot accidentally become disengaged from the bag. Thus the possibility of the mechanism becoming separated from the bag and permitting uncontrolled flow of urine from the outlet port is eliminated. In addition, the outlet tube devices 50, 150, 280, and 380 of the present invention eliminate the need to store the free end of the outlet tube in a keeper when not in use, thereby eliminating the possibility of the outlet tube springing outward in such a manner as to flick droplets of residual urine on the attending medical personnel. Further the lower ends of the jaws 54A, 54B of the device 50, the skirt 166 of the device 150, the skirt 266 of the device 280, and the skirt 410 of the device 380 all serve as a shield to prevent the hands of the user from accidentally coming into direct contact with the ends of the discharge tubes 66, 168, 284, and 414. Finally the devices 50, 150, 280, and 380 are all inexpensive to manufacture and provide one-step operation which can be performed quickly and with only one hand.

While the foregoing embodiments have been disclosed with respect to a urinary drainage bag 10 having a urine meter 30 disposed on its front face, it will be appreciated that the urine meter is not a part of the present invention and that the outlet tube devices 50, 150, 280, and 380 may be used on any urinary drainage bag which comprises an outlet port. It will further be understood that the invention is not limited to urinary drainage bags and that the outlet tube devices 50, 150, 280, and 380 may also be suitable for use on other types of containers for collecting biological fluids.

Finally, it will be understood that the preferred embodiment has been disclosed by way of example, and that other modifications may occur to those skilled in the art without departing from the scope and spirit of the appended claims.

What is claimed is:

1. A container for collecting biological fluids comprising:
   walls comprised of a fluid-impervious material defining a fluid-tight chamber therewithin;
   a main body portion fixedly mounted to said bag,
   a pair of jaws mounted to said base member and pivotable with respect to one another, each of said pair of jaws having upper and lower ends, said pair of jaws having mutually facing clamping members adjacent said lower ends, and said pair of jaws further comprising biasing means operatively associated with said pair of jaws for biasing said clamping members of said pair of jaws toward one another, said clamping members of said pair of jaws being separable by squeezing said upper ends of said pair of jaws; and
   a compressible, resilient tube having an upstream end in fluid communication with said chamber at a lower portion thereof, said tube extending between said clamping members of said pair of pivotably mounted jaws, and a downstream end of said tube being disposed to discharge a fluid from said container;
   whereby when said clamping members of said pair of jaws are biased toward one another, said clamping members of said pair of jaws compress and occlude said tube, and whereby an operator may selectively separate said clamping members of said pair of jaws to permit said tube to open to drain a fluid collected within said chamber of said container without having to move or to touch said drainage tube.

2. The container of claim 1, further comprising latch means selectively operable to maintain said lower ends of said pair of jaws in an open state, whereby fluid flow is permitted to continue without said upper ends of said pair of jaws being squeezed.

3. The container of claim 2, wherein said latch means comprises a latch arm pivotably mounted to one of said pair of jaws adjacent said upper end thereof, said latch arm having a flange formed at a free end thereof, said other of said pair of jaws having a keeper formed thereon such that said flange on said latch arm engages said keeper on said other of said pair of jaws to retain said pair of jaws in said open state.

4. The container of claim 1, further comprising a skirt which envelopes said downstream end of said tube so as to prevent accidental contact by an operator with said downstream end of said tube.

5. The container of claim 4, wherein said skirt that envelopes said downstream end of said tube comprises said lower ends of said pair of jaws extending beyond and enveloping said downstream end of said tube.

6. A container for collecting biological fluids comprising:

walls comprised of a fluid-impervious material defining a fluid-tight chamber therewithin;

a rigid housing fixedly attached to one of said walls, said rigid housing having an opening therein;

a compressible, resilient tubing defining a fluid passage through said rigid housing, said fluid passage having an upstream end and a downstream end, said upstream end of said fluid passage being in fluid communication with said chamber, and said downstream end of said fluid passage being disposed to discharge a fluid from said container;

a clamp captured within said rigid housing and having opposed pinch jaws selectively operative to clamp said tubing so as to occlude fluid flow therethrough, and said clamp being selectively operative through said opening in said rigid housing to unclamp said tubing to permit a fluid contained within said chamber to flow through said fluid passage to be discharged from said container;

whereby an operator may selectively operate said clamp to drain a fluid collected within said chamber of said container without having to move or to touch said tubing.

7. The container of claim 6, wherein said rigid housing comprises a door member formed in said housing, said door member being selectively openable to facilitate placement of said length of compressible, resilient tubing within said housing, and said door member being selectively closable after said length of compressible, resilient tubing has been placed within said housing so as to secure said length of tubing within said housing.

8. The container of claim 6, further comprising a skirt enveloping said downstream end of said flexible tubing so as to prevent accidental contact by an operator with said downstream end of said flexible tubing.

9. The container of claim 8, wherein said skirt comprises an extension of said rigid housing.

\* \* \* \* \*